(12) United States Patent
Tang et al.

(10) Patent No.: US 12,029,796 B2
(45) Date of Patent: Jul. 9, 2024

(54) FLUORESCENT PROBES FOR SILVER ION DETECTION

(71) Applicant: THE HONG KONG UNIVERSITY OF SCIENCE AND TECHNOLOGY, Hong Kong (CN)

(72) Inventors: Benzhong Tang, Hong Kong (CN); Sijie Chen, Hong Kong (CN); Sheng Xie, Hong Kong (CN); Wenxiong Wang, Hong Kong (CN); Neng Yan, Hong Kong (CN); Alex Yu Hin Wong, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 607 days.

(21) Appl. No.: 16/761,602

(22) PCT Filed: Nov. 7, 2018

(86) PCT No.: PCT/CN2018/114289
§ 371 (c)(1),
(2) Date: May 5, 2020

(87) PCT Pub. No.: WO2019/091389
PCT Pub. Date: May 16, 2019

(65) Prior Publication Data
US 2021/0170053 A1 Jun. 10, 2021

Related U.S. Application Data

(60) Provisional application No. 62/707,532, filed on Nov. 7, 2017.

(51) Int. Cl.
A61K 49/00 (2006.01)
G01N 21/64 (2006.01)

(52) U.S. Cl.
CPC ..... A61K 49/0023 (2013.01); G01N 21/6428 (2013.01); G01N 2021/6439 (2013.01)

(58) Field of Classification Search
CPC ............... A61K 49/00; A61K 49/0023; G01N 21/6428; G01N 21/64; G01N 2021/6439; C09K 11/06; C07D 257/04
USPC ................................ 424/1.11, 1.65, 9.1, 9.6
See application file for complete search history.

(56) References Cited

FOREIGN PATENT DOCUMENTS

WO 2015164784 A1 10/2015
WO WO-2015164784 A1 * 10/2015 ............. C07F 3/003

OTHER PUBLICATIONS

Xie, Sheng et al. "Fluorogenic Ag+-Tetrazolate Aggregation Enables Efficient Fluorescent Biological Silver Staining", Angewandte Chemie, International Edition, vol. 57, No. 20, Apr. 14, 2018, pp. 5750-5753.
Yan, Neng et al. "real-time Monitoring of the Dissolution Kinetics of Silver Nanoparticles and Nanowires in Aquatic Environments Using an Aggregation-Induced Emission Fluorogen" vol. 54, No. 36, Apr. 9, 2018, pp. 4585-4588.
Bian, Ning et al. "Imidazole-Bearing Tetrapheny lethylene: Fluorescent Probe for Metal Ions Based on AIE Feature", New Journal of Chemistry, vol. 35, No. 8, Jun. 14, 2011, pp. 1667-1671.
Ye, Jiahai et al. "A New Ratiometric Ag+Fluorescent Sensor Based on Aggregation-Induced Emission"., Tetrahedron Letters, vol. 53, No. 29, Nov. 29, 2011, pp. 593-596.

* cited by examiner

*Primary Examiner* — D. L. Jones
(74) *Attorney, Agent, or Firm* — Nath, Goldberg & Meyer; Joshua B. Goldberg

(57) ABSTRACT

Fluorescent probes for silver ion detection include organic, water-soluble compounds having aggregation-induced emission (AIE) characteristics. The probes can sense or detect silver ions through aggregation or a precipitation reaction between the silver ions and the organic compounds which induces fluorescence. The compounds are acidic, soluble in aqueous phase, and provide low background fluorescence in aqueous solutions.

12 Claims, 8 Drawing Sheets

FLUORESCENT PROBES FOR SILVER ION DETECTION

FIELD

The present subject matter relates generally to a series of compounds for fluorescent silver metal ion detection and their applications in biological fluorescent silver staining, including in-gel protein detection.

BACKGROUND

Silver materials are useful in a variety of applications. Silver is used in electrical contacts and conductors due to its excellent thermal and electrical conductivity. Silver is also used in specialized mirrors, window coatings, and in catalysis of chemical reactions. As photon-sensitive materials, silver compounds are used in photographic and X-ray films. Silver salts and silver nanomaterials are used as antibacterial materials and have been incorporated in food packaging, cosmetics, and medical devices (for example bandages and wound-dressings). Production processes involving the use of silver-containing materials result in wastes containing silver ions. Since silver ions are toxic to organisms, monitoring the quantity of silver ions present in industrial waste is important for sustainable development.

The distribution of silver ions in the environment is worthy of concern. Generally, silver ions are present in the environment in low concentrations at most since they have a high affinity to a range of chemical structures and are prone to be in the form of salts, oxides or metallic species. In the environment, ionic silver is typically immobilized to a large extent as a sparingly soluble salt like AgCl or $Ag_2S$. Besides, average silver concentrations in natural waters are typically 0.2~0.3 µg/L. However every year, large amounts of silver are released to the environment from industrial wastes created in industries such as electronics, photography, mirrors, and pharmacy.

Silver and its complexes are highly toxic to microbial bacteria, algae, and fungi. The toxicity of silver is largely attributed to silver ions which bind to and inactivate a range of biological molecules (DNA/Protein). Toxic concentrations and inhibitory concentrations for microbes are typically in the range of 0.1 mg/L to 20 mg/L. As such, treatment of silver-containing waste in the production process is important. Silver-containing anti-bacterial products can release a significant amount of silver into the environment, thereby posing a high threat to environmental microbes.

Silver ions, in certain circumstances, are also toxic to human beings. Although silver materials have long been recognized as non-toxic to human kind, a high content of silver ions can be a threat to human health. In fact, many silver-containing products can release silver ions, including highly corrosion-resistant metallic silver. In a toxicity study, the LD50 value for mice was found to be in the order of 50~100 mg/kg for soluble silver salts, which is much lower than other heavy metal ions but still significant. In a WHO report, it was reported that most foods contain traces of silver in the 10~100 mg/kg range. In the long run, accumulation of silver in the body leads to negative effects, including blood silver and urine silver excretion, cardiac enlargement, growth retardation and degenerative changes. Also, insoluble $Ag^+$ precipitates may damage skin and eyes. Ionic silver is reported to displace essential metal ions including $Ca^{2+}$ and $Zn^{2+}$ in bones. Further, accumulated silver inside a human body can also disrupt the body's microbial system.

Detection of silver ion concentration is also an important aspect of evaluating drug efficacy. Silver products have been widely used as antibacterial materials in recent years, which have been largely ascribed to the function of silver ions. Silver ions irreversibly bind to the key enzyme systems in the cell membranes of pathogens. The detailed action process of their antibacterial effect, however, is not yet clear. Soluble silver compounds can be used as external antiseptic agents (15-50 µg/L), as bacteriostatic agents (up to 100 µg/L), and as disinfectants (>150 µg/L). The silver ion solutions are used directly as medicine. For example, silver nitrate solutions are used as disinfectants and microbiocides in bandages, wound-dressings, and other medical instruments. Silver sulfadiazine (silvadene) was widely used as a topical cream on burns.

Monitoring silver ion release from antibacterial silver-containing materials is important for their quality control. Recently, silver nanomaterials have also been proposed as a novel antibacterial agent with broad spectrum. Silver nanomaterials serve as a pool of silver ions for long term release. In all of these applications, means for detection of silver ion concentrations have been in demand not just for quality control, but also for tracking environmental protections. Metallic silver, silver nanoparticles, and sparingly soluble silver salts release silver ions when they come in contact with water. The release kinetics depend on the size of the nanoparticles, their surface functionalization, the temperature, and the composition of the surrounding medium.

In recent years, silver nanomaterials and coatings have been used as efficient antimicrobial reagents with a broad anti-microorganism spectrum, for example anti-contamination of healthcare products (cosmetics), medical products (bandages), fresh food (food packaging). Previous studies suggested that antimicrobial efficacy is largely attributed to the silver ions released from the metallic silver materials. Furthermore these silver-containing products end up in the environment, causing a potentially negative impact on many living organisms. In this sense, monitoring the time-dependent release of soluble $Ag^+$ from silver-containing products can be useful for quality control production of antibacterial silver materials, the study of toxicity of silver in the environment, and for antibacterial processes.

The wide use of silver antibacterial materials in recent years raises a public concern of (silver-containing) drug-resistant pathogens, albeit less significant than other antibiotics-induced resistance. As such, it has become increasingly important to monitor the release of silver ions from these materials. Biological silver staining is one method used for this purpose.

Silver salts are commonly used in analysis of biochemical samples. In biomedical labs, silver staining has been an accurate, daily, and cheap staining protocol for proteins, nucleic acids, lipopolysaccharides, glycoproteins and polysaccharides in gel electrophoresis. In such protocols, silver ions are first impregnated into biological samples, which are later reduced to metallic silver to give visualization. The chromogenic process is due to the formation of silver nanoparticles of >10 nm. Thus, these silver staining protocols generally provide low reproducibility.

The detection of silver species can also occur using one of various instrumental techniques such as flame atomic absorption spectrometry (FAAS), graphite furnace atomic absorption spectrometry (GFAAS), inductively coupled plasma atomic emission spectrometry (ICP-AES), inductively coupled plasma mass spectrometry (ICP-MS), and electro-chemical assay. For example, the detection limit of atomic absorption spectroscopy (graphite furnace) is 2 µg/L, and of neutron activation analysis, is 2 ng/L. However, these protocols are typically tedious and often require expensive and specialized instruments.

Optical spectroscopical methods have advantages for their simplicity. They involve molecular probes which contain silver ion binding units and an optical-active unit for detection. As an example, the spectrographic and colorimetric method with dithizone has a detection limit of 10 μg/L.

Detection by fluorescence generally has high sensitivity and selectivity. Many fluorescent probes for silver detection have been previously reported. Use of traditional organic luminogens, however, is greatly limited by the aggregation caused quenching (ACQ) effect. Traditional organic luminogens are highly emissive in dilute solution, but become weakly emissive or non-emissive in high concentration solution when aggregated or in the solid state.

Accordingly, organic luminogens for sensing silver ions are highly desirable.

SUMMARY

Fluorescent probes for silver ion detection include organic, water-soluble compounds having aggregation-induced emission (AIE) characteristics. The probes can sense or detect silver ions through aggregation or a precipitation reaction between the silver ions and the organic compounds which induces fluorescence. The compounds are acidic, soluble in the aqueous phase, and provide low background fluorescence in aqueous solutions.

In an embodiment, the compounds have a backbone structural formula selected from the group consisting of:

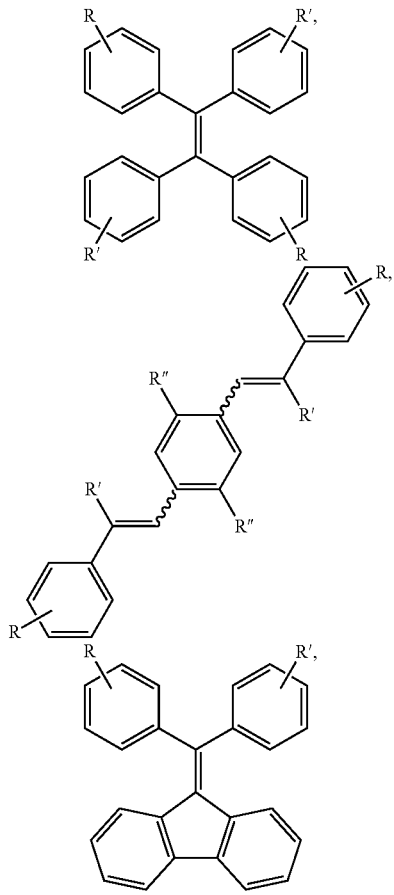

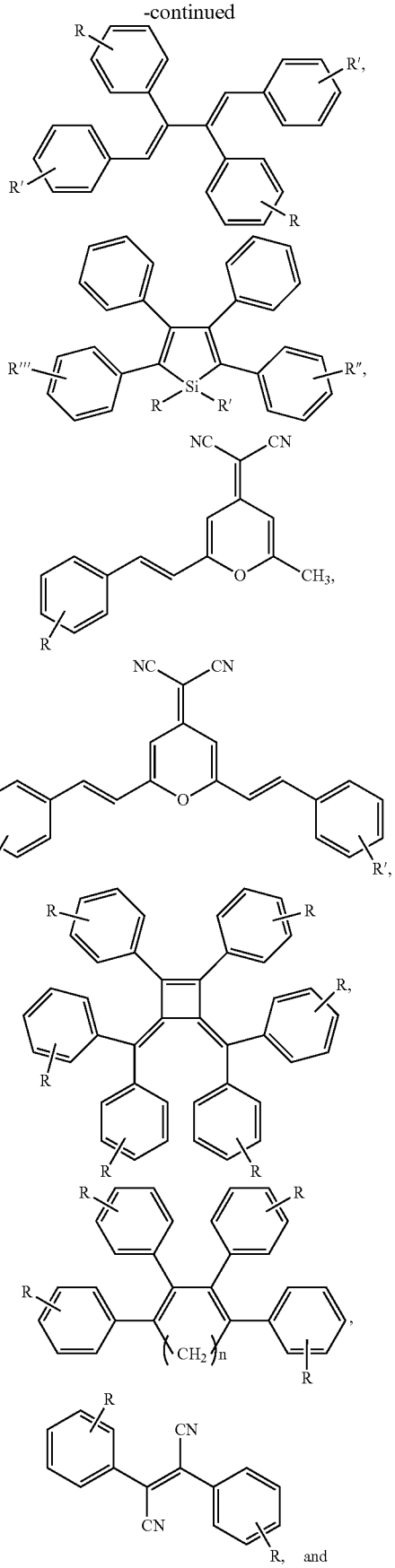

-continued

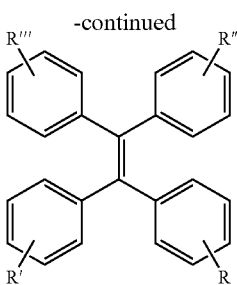

wherein at least one of R, R', R" or R'" is selected from the group consisting of

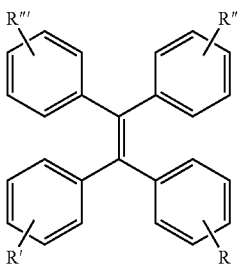

and wherein all other of the R, R', R", and, R'" groups are selected from the group consisting of H, heteroatom, alkyl, unsaturated alkyl, heteroalkyl, cycloalkyl, heterocycloalkyl, aryl, and heteroaryl.

In a further embodiment, the compounds have the backbone structural formula:

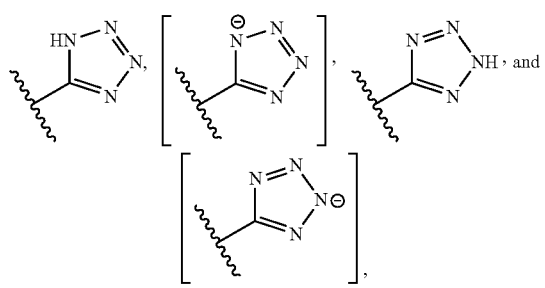

wherein at least one of R, R', R" or R'" is selected from the group consisting of

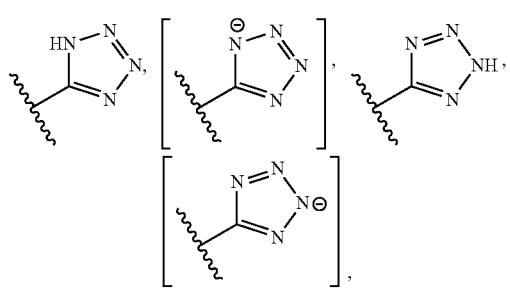

and wherein all other of the R, R', R", and, R'" groups are selected from the group consisting of H, heteroatom, alkyl, unsaturated alkyl, heteroalkyl, cycloalkyl, heterocycloalkyl, aryl, and heteroaryl.

In an embodiment, the compound is selected from:

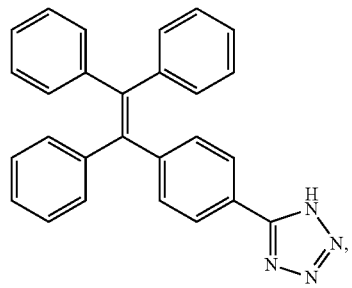

TPE-1TTZ

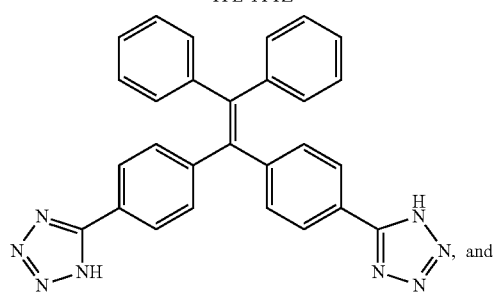

TPE-2TTTZ

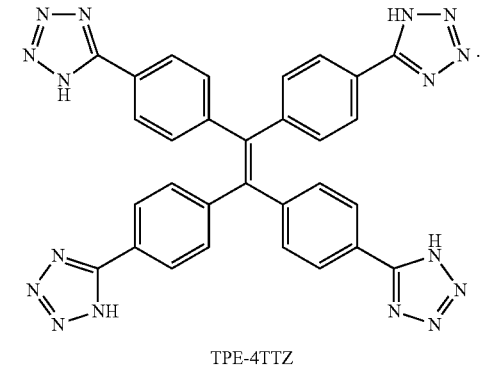

TPE-4TTZ

BRIEF DESCRIPTION OF DRAWINGS

Various embodiments will now be described in detail with reference to the accompanying drawings.

FIG. 3A depicts UV-Vis spectrum indicating complexion of the compound (5 μM) with Ag$^+$ (100 μM) in water; FIG. 3B depicts emission of the compound (5 μM) in water with or without Ag$^+$ (100 μM); FIG. 3C depicts emission of the compound (5 μM) in water with different increasing equivalence of Ag$^+$; FIG. 3D depicts emission intensity at 506 nm to the ratio of Ag$^+$ and the compound (5 μM), with data obtained from FIG. 3C.

FIG. 4A depicts emission of the compound (5 μM) in water with or without Ag$^+$ (100 μM); FIG. 4B depicts emission of the compound (5 μM) in water with different increasing equivalence of Ag$^+$; FIG. 4C depicts emission intensity at 489 nm for the ratio of Ag$^+$ and the compound (5 μM), with data from FIG. 4B.

FIG. 5A shows emission of the compound (5 μM) in water with or without Ag$^+$ (100 μM); FIG. 5B shows emission of the compound (5 μM) in water with different increasing equivalence of Ag$^+$; FIG. 5C shows emission intensity at 490 nm to the ratio of Ag$^+$ and the compound (5 μM), with data from FIG. 5B.

FIG. 6A depicts fluorescence emission spectra of TPE-4TTZ in phosphate aqueous solution (10 mM, pH 7.4) with or without metal ions (10 μM); FIG. 6B depicts variation of the fluorescence intensity at 502 nm ($I_{502}$ nm) of compound TPE-4TTZ in H$_2$O in the presence of 4.0 equiv. of the respective metal ions.

FIG. 10B: 20 nm citrate coated AgNPs; FIG. 10C: 60 nm AgNPs Tween-20 coated AgNPs) by TPE-4TTZ fluorescent detection and the conventional ICP-MS detection after ultrafiltration.

DETAILED DESCRIPTION

Definitions

Figure 1A:
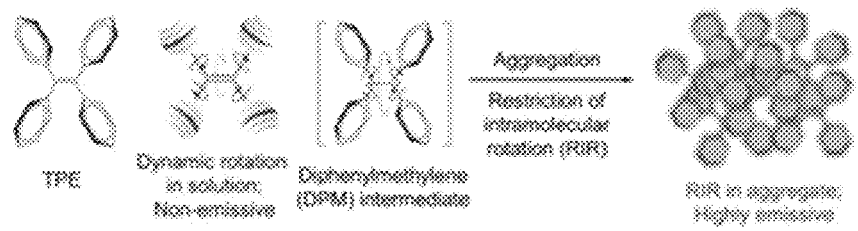
FIG. 1A is a diagram depicting the propeller-shaped luminogen tetraphenylethylene (TPE).

The following definitions are provided for the purpose of understanding the present subject matter and for constructing the appended patent claims.

It is noted that, as used in this specification and the appended claims, the singular forms "a", "an", and "the" include plural references unless the context clearly dictates otherwise.

The term "$\lambda_{ex}$" as used herein refers to excitation wavelength.

The phrase "aggregation caused quenching" or "ACQ" as used herein refers to the phenomenon wherein the aggregation of π-conjugated fluorophores significantly decreases the fluorescence intensity of the fluorophores. The aggregate formation is said to "quench" light emission of the fluorophores.

The phrase "aggregation induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

"Emission intensity" as used herein refers to the magnitude of fluorescence/phosphorescence normally obtained from a fluorescence spectrometer or fluorescence microscopy measurement; "fluorophore" or "fluorogen" as used herein refers to a molecule which exhibits fluorescence; "luminogen" or "luminophore" as used herein refers to a molecule which exhibits luminescence; and "AIEgen" as used herein refers to a molecule exhibiting AIE characteristics.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

As used herein, a "donor" material refers to an organic material, for example, an organic nanoparticle material, having holes as the majority current or charge carriers.

As used herein, an "acceptor" material refers to an organic material, for example, an organic nanoparticle material, having electrons as the majority current or charge carriers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Compounds

Aggregation-induced emission is a relatively new concept of responsive fluorescence. Unlike conventional luminophores, a typical AIE luminogen such as tetraphenylethylene (TPE) has a propeller-shaped, non-planar structure. In dilute solution, TPE molecules undergo intermolecular rotation, which consumes energy through non-radiative pathways and renders them non-luminescent. In the aggregated state, intermolecular rotations are restricted on account of the physical constraint from neighboring molecules (FIG. 1A).

Due to their facile synthesis and outstanding performance, TPE and its derivatives have been widely used to construct AIE luminogens for various applications, including chemosensing, bioimaging and smart optical materials. Some AIE luminogens for metal ion sensing, however, have had some difficulty in sensing silver ions.

Accordingly, the present subject matter contemplates organic, water-soluble compounds having aggregation-induced emission (AIE) characteristics. The compounds, also referred to herein as "tetrazole-functionalized AIE luminogens," or "fluorescent probes" can sense or detect silver ions through aggregation or a precipitation reaction between the silver ions and the organic compounds which induces fluorescence. The compounds are acidic, have good solubility in the aqueous phase (in particular when a salt is formed in basic conditions), and provide low background fluorescence in aqueous solutions.

According to an embodiment, the compounds have a backbone structural formula selected from the group consisting of:

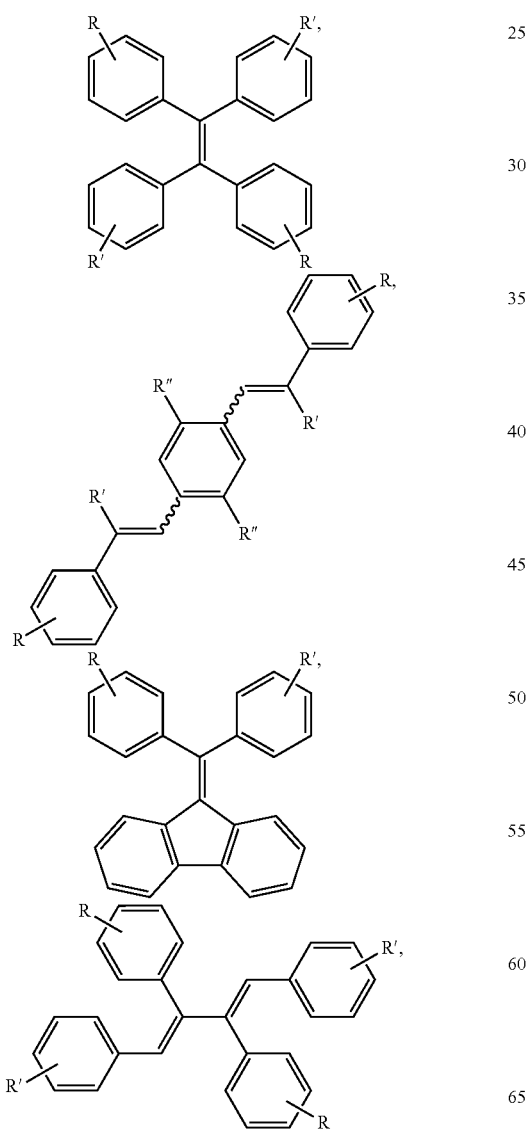

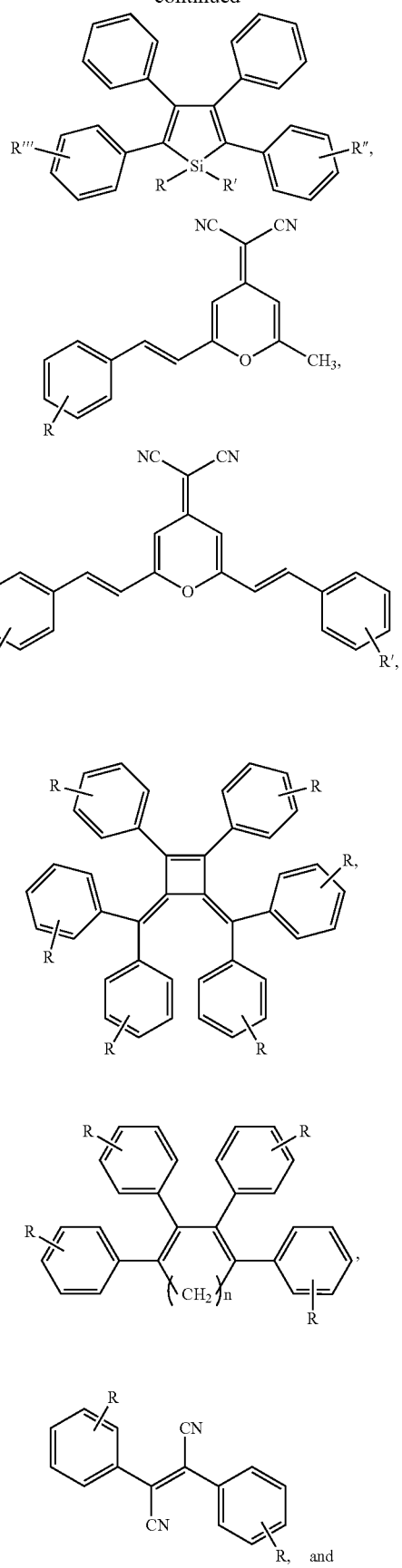

-continued

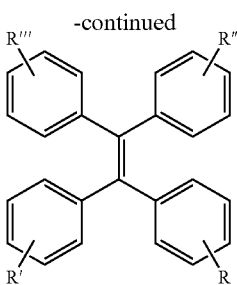

wherein at least one of R, R', R" or R'" is selected from the group consisting of

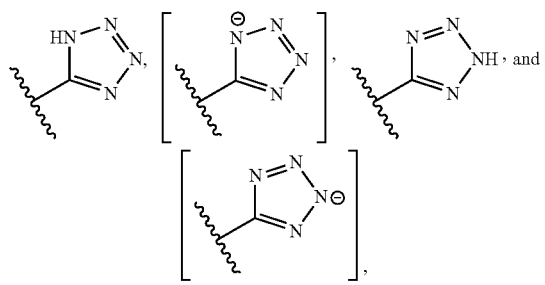

and wherein all other of the R, R', R" and R'" groups are selected from the group consisting of H, heteroatom, alkyl, unsaturated alkyl, heteroalkyl, cycloalkyl, heterocycloalkyl, aryl, and heteroaryl.

According to an embodiment, the compounds have the following backbone structural formula:

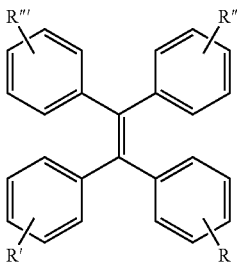

wherein at least one of R, R', R" or R'" is selected from the group consisting of

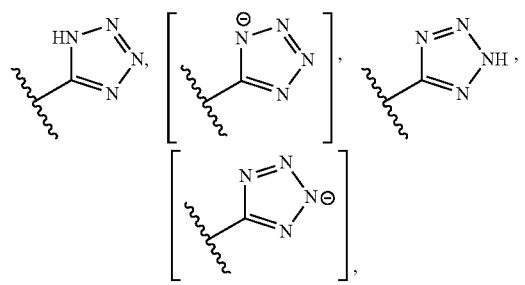

and wherein all other of the R, R', R" and R'" groups are selected from the group consisting of H, heteroatom, alkyl, unsaturated alkyl, heteroalkyl, cycloalkyl, heterocycloalkyl, aryl, and heteroaryl.

In an embodiment, the compounds are selected from:

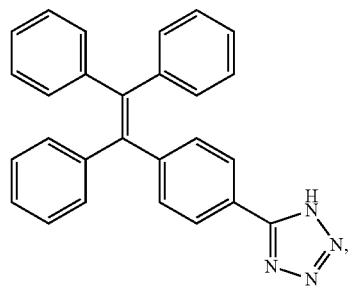

TPE-1TTZ

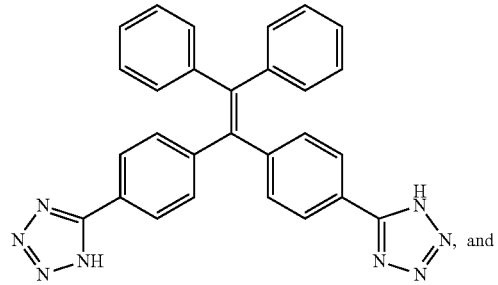

TPE-2TTZ

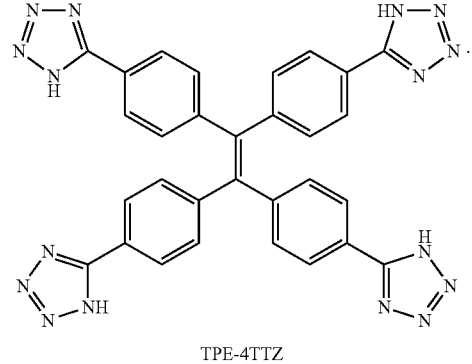

TPE-4TTZ

Synthesis

Synthesis of the compounds can be straightforward and accomplished using various synthetic pathways. Exemplary reaction schemes for preparing the present compounds are provided below:

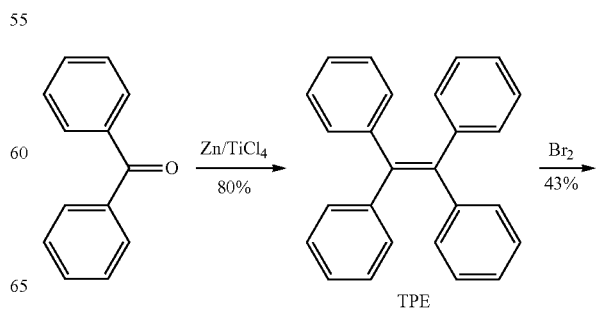

TPE

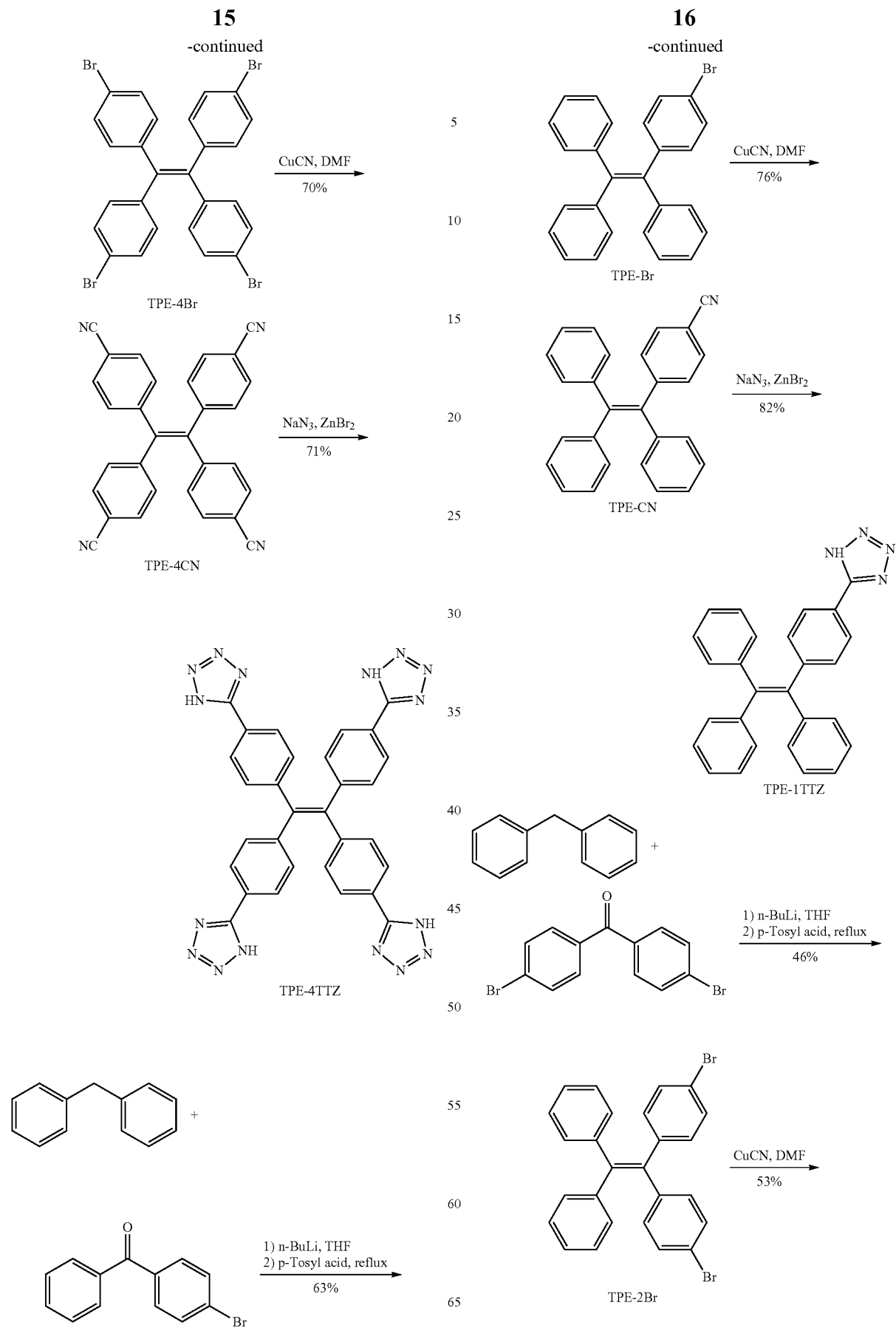

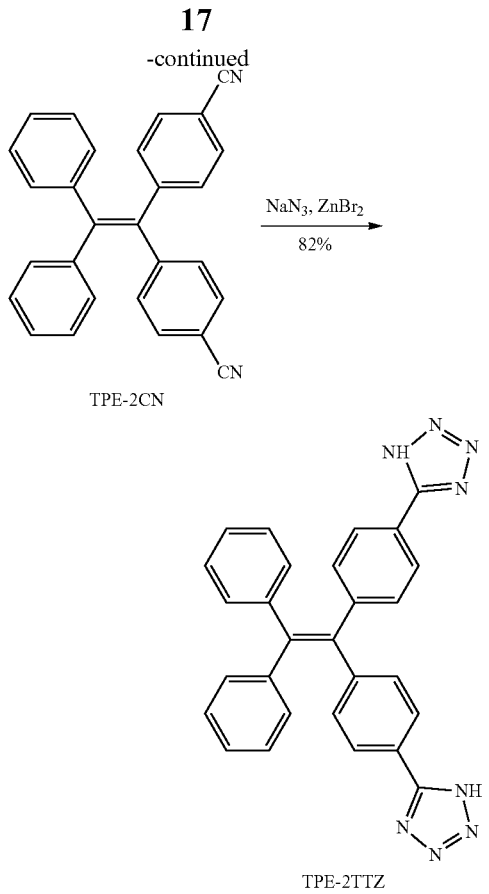

Brominated TPEs (TPE-Br and TPE-2Br) can be synthesized from diphenylmethane and corresponding brominated biphenyl ketone following a procedure reported in *J Org Chem* 2007, 72, 8054. TPE-4Br synthesis can include bromination of TPE, which can be accessed by the McMurry coupling of benzophenone in good yields. The addition of liquid bromide to TPE is an aromatic bromination. These brominated TPE derivatives can undergo nucleophillic aromatic substitution by using copper cyanide (CuCN) as the nucleophile in DMF at elevated temperatures, which results in replacement of the Br atoms with a —CN group. These CN-derivatized TPEs can be isolated at modest yields. In the final step, these CN-derivatized TPEs (TPE-CN, TPE-2CN and TPE-4CN) can be cycloadded with azido ions ($N_3^-$) to give the targeted tetrazole-tagged TPEs in good yields. The overall protocol to synthesize these tetrazole-derivatized TPEs is simple, efficient and does not require harsh conditions and specific reagents.

In an exemplary embodiment, the tetrazole functional moieties can be installed using a nitrile-azide cycloaddition, as shown below, with CN compounds accessed in stock or through the substitution reaction of halogen-substituted compounds:

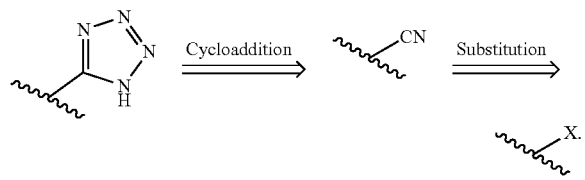

AIE Activity

The present compounds are strongly emissive in the solid state with good fluorescent quantum yields. The compounds are weakly emissive or non-emissive when dissolved in aqueous solutions. As described in detail herein, for example, TPE-1TTZ, TPE-2TTZ, and TPE-4TTZ exhibit strong blue-green emission with good fluorescent quantum yields (Qy: TPE-1TTZ 39.6%; TPE-2TTZ 36.2%; TPE-4TTZ 76.8%) in the solid state. In contrast, when these compounds are dissolved, the solutions only emit faint light (Qy<1%). The compounds dissolve well in alcohols. The compounds can be modestly dissolved (for TPE-4TTZ, up to 100 μM in DI-water) in the aqueous phase. Furthermore by the addition of NaOH solutions, the formed salts dissolve well in the aqueous phase (for TPE-4TTZ, up to 1 M in water). The freely-dissolved aqueous solutions are not emissive, which further demonstrates the AIE properties of the present compounds.

Reaction with Silver

Figure 1B:
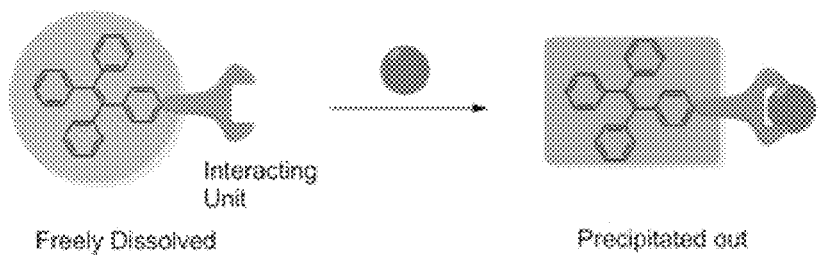
FIG. 1B is a diagram depicting the design of the silver ion sensor and modulation of the aggregation-state of the probes by metal ions.

As shown in FIG. 1B, the tetrazole group in the present compounds serves as the silver interacting group, while the TPE core endows the responsive AIE fluorescence. The tetrazole-functioned moieties can 'extract' out silver ions as white solids in a silver-tetrazole precipitation reaction, as shown below.

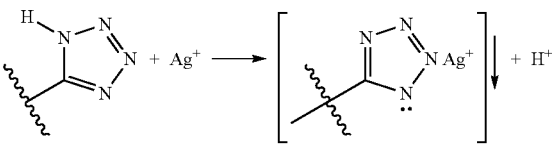

Tetrazole exists in two tautomeric forms (1H and 2H) and the two forms are in dynamic equilibrium. The resulting tetrazole-silver complexes are believed to exist in a polymeric coordination network, with silver binding in a mono-, bi- or tri-dentate format to the nitrogen centers through coordination. The complexes are sparingly soluble in many solutions.

Silver Detection

A method of detecting for presence of silver ions in a solvent can include contacting one or more of the tetrazole-functionalized AIE luminogens with a solvent and irradiating the solvent with ultraviolet light. An observable emission can indicate the presence of silver ions. The solvent can include at least one of natural water, industrial wastes, aqueous buffer solutions, and biological samples. According to an embodiment, the solvent has a pH>4.

A method of imaging ionic silver in vivo can include administering one or more of the tetrazole-functionalized AIE luminogens to an organism and obtaining images of the organism while the compound is within the organism using fluorescence imaging.

Figure 2A:
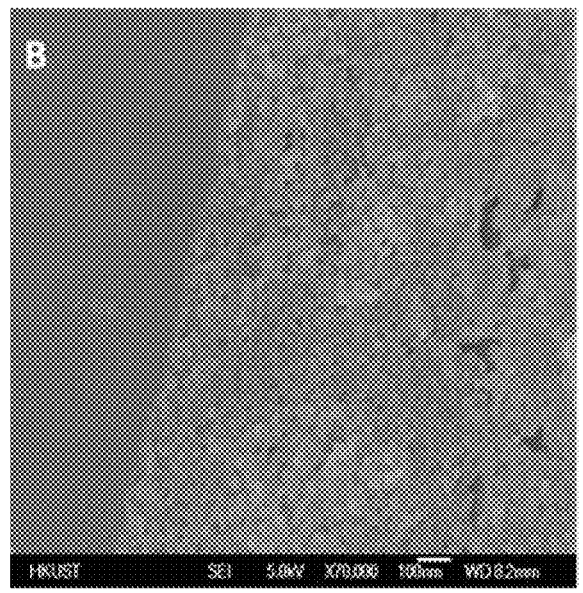
FIG. 2A is a scanning electron microscopy (SEM) image revealing the formation of evenly distributed nanoparticles of silver coordination polymers.
Figure 2B:
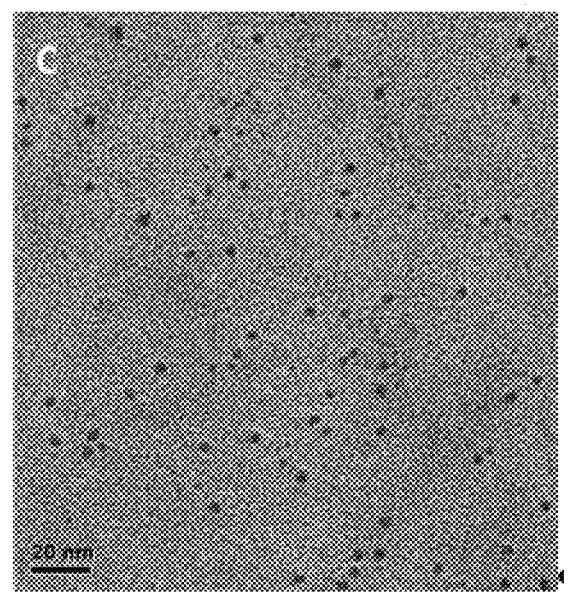
FIG. 2B is a transmission electron microscopy (TEM) image showing tiny dots (metallic silver dots) in black which are reduced from the coordinating polymer by strong electron-beam irradiation.

When non-emissive aqueous solutions including TPE-4TTZ (e.g., 5 μM) were treated by addition of silver ions (e.g., 500 μM) and irradiated with UV light (e.g., under hand-held UV-lamp 350 nm irradiation), the solution became highly emissive. The turn-on fluorescence response was instant. The detection of silver ions was highly sensitive and sharp intensity changes could be detected with the naked eye. DLS (Dynamic light scattering) measurement confirmed the formation of nanoparticles. After evaporation of the fluorescent liquid, nano-sized particles (d=5~30 nm) with even distribution were observed in SEM (FIG. 2A). A further characterization in TEM did not show the corresponding particles, but detected metallic silver dots (d=2~5 nm) instead (FIG. 2B). This is likely due to the reduction of silver-tetrazole complexes by the strong electron-beam during TEM studies. These emissive silver-compound solid complexes are hardly soluble in a range of solvents, including DMSO, methanol, and water. NMR analysis of these complexes is not possible. The complexes are also resistant to acid/base treatment, or heating by a heat-gun.

Referring to the above design, the tetrazole-$Ag^+$ interaction mode below is proposed to explain the formation of a silver-TPE-4TTZ polymeric complex and result in silver ion detection in these cases.

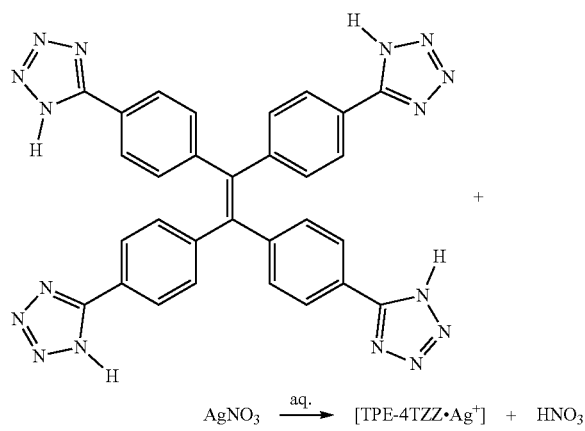

According to this model, silver ions in the solution undergo instant chelation with tetrazole units of the AIE probes. The chelation bridged by $Ag^+$ then results in hardly soluble species for TPE-1TTZ, and/or most likely metallo supramolecular polymers when compound TPE-2TTZ and compound TPE-4TTZ are used. These species could efficiently form clusters, i.e., aggregates. As a result, these AIE-active molecules within aggregates show restricted motions, which lead to efficient emission.

Figures 3A, 3B, 3C, 3D:
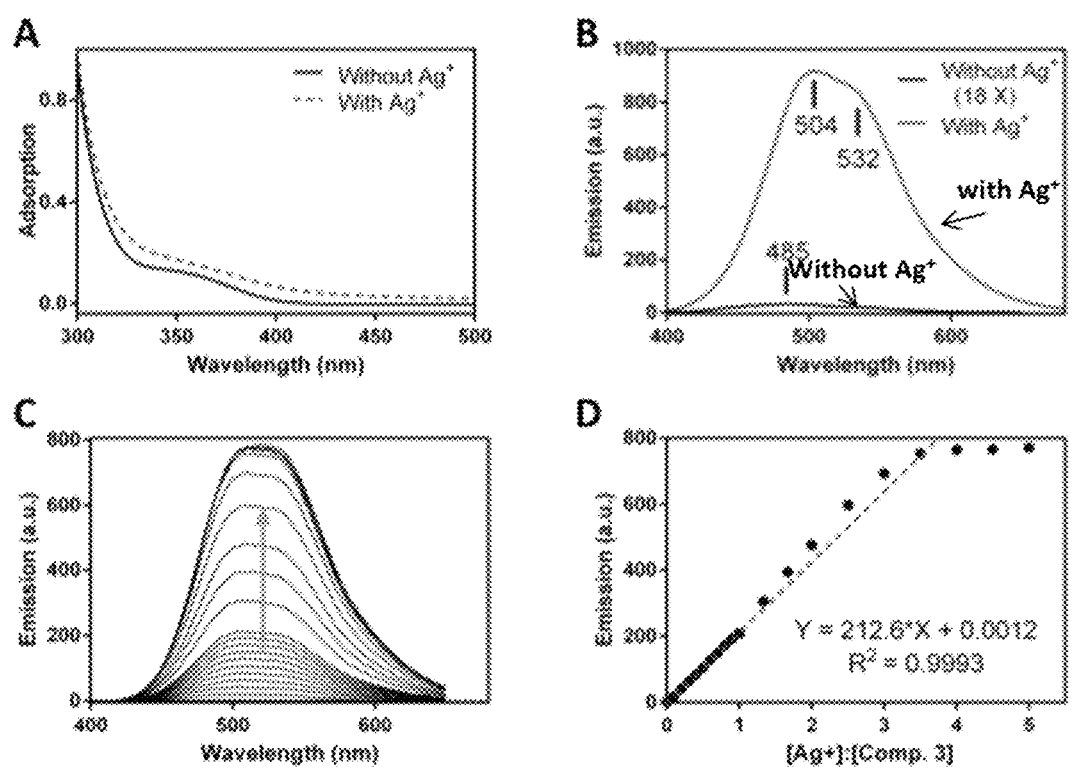
FIGS. 3A-3D are graphs depicting silver sensing properties of TPE-4TTZ (excitation wavelength: 345 nm)
Figures 4A, 4B, 4C:
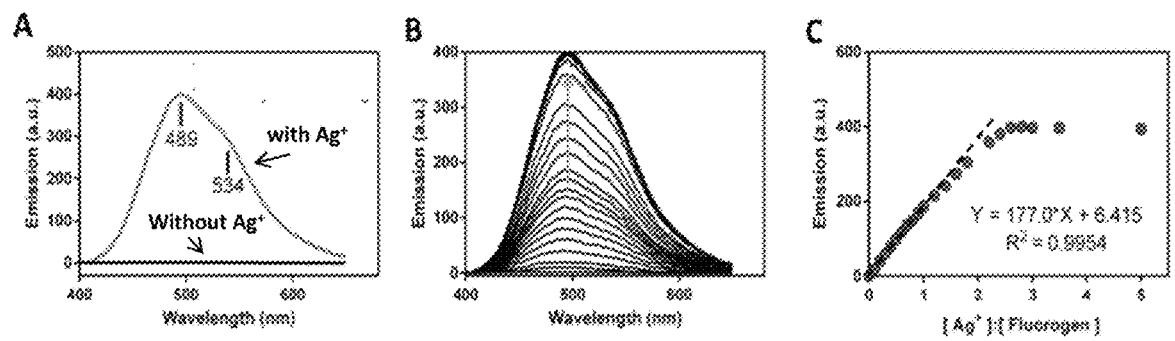
FIGS. 4A-4C are graphs depicting silver sensing properties of TPE-2TTZ (excitation wavelength: 345 nm)
Figures 5A, 5B, 5C:
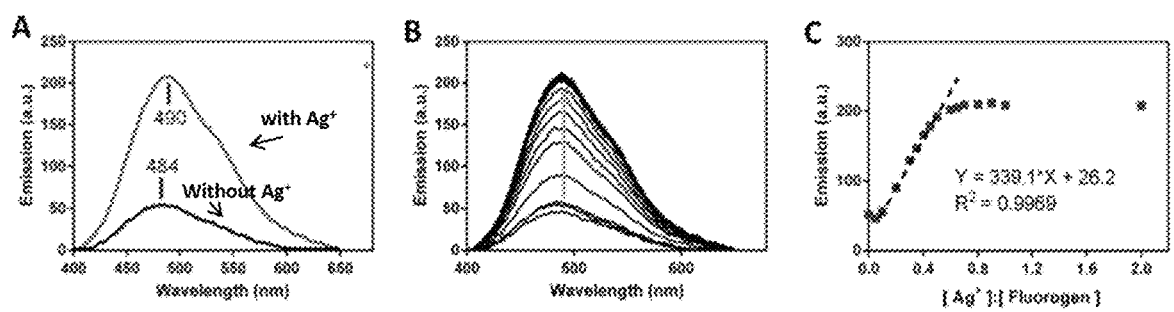
FIGS. 5A-5C are graphs depicting silver sensing properties of TPE-1TTZ (Excitation wavelength: 345 nm)

In fluorescence spectroscopy, solutions containing silver ions behaved quite differently from solutions without silver ions in terms of intensity, with the ratio of intensity at maximum peak at 504 nm exceeding 400 times (FIGS. 3A-3D). Compounds TPE-1TTZ and TPE-2TTZ responded to silver ions similarly with enhanced fluorescence, as shown in FIGS. 4A-4C and FIGS. 5A-5C. All of the three silver-containing fluorescent solutions revealed similar maximum emission wavelength (TPE-1TTZ 490 nm; TPE-2TTZ 489 nm; TPE-3TTZ 504 nm). Titration studies indicated that the emission intensity of metal-compound mixture increases with the addition of silver ions (FIGS. 3C, 4B and 5B). By plotting the intensity of maximum intensive peaks against the ratio of ion concentrations, it was expected that the working curve for the quantitative detection of silver ions could be established. For example, when the corresponding peak intensities (504 nm) versus the concentration of silver ions were plotted, a linear relationship was displayed ranging from 0.04 to 15 µM with the square of correlation coefficient equal to 0.9993 (FIG. 3D). Meanwhile, the detection limit (LOD) of silver ions is estimated to be 40 nM (S/N=3 and n=11). With a further increase of [$Ag^+$], the intensity reaches a plateau. Similar results were observed for compound TPE-2TTZ (FIGS. 4A-4C) and compound TPE-1TTZ (FIGS. 5A-5C). The performance of the three probes for silver detection is summarized in Table 1.

TABLE 1

Summary of silver sensing parameters.

| | Excitation (nm) | Emission (nm) | LOD (nM) | Linear Range (µM) |
|---|---|---|---|---|
| TPE-1TTZ | 345 | 490 | 1.5 | 0.1~3 |
| TPE-2TTZ | 345 | 489 | 3.0 | 0.2~10 |
| TPE-4TTZ | 345 | 504 | 2.3 | 0.04~15 |

LOD: limit of detection. Probes: 5 µM in DI-water. Measured by a Perkin-Elmer LS 55 spectrofluorometer.

A saturated PL intensity plateau was observed for all of the luminogens. The PL intensity is saturated when the ratio of [$Ag^+$]:[TPE-4TTZ] approaches 4, and reaches maximum intensity when [$Ag^+$]:[TPE-2TTZ] is 2.6 and [$Ag^+$]:[TPE-1TTZ] is 0.6. This reveals that the maximum linear detection concentration of [$Ag^+$] is related to the number of tetrazole moieties in the TPE-cored molecular probes. This is reasonable in view of the stoichiometric coordination interactions. The linear detection range is thus dependent on the concentration of the probe and can be further expanded by setting the concentrations of the probes (Table 1).

Figure 6A:
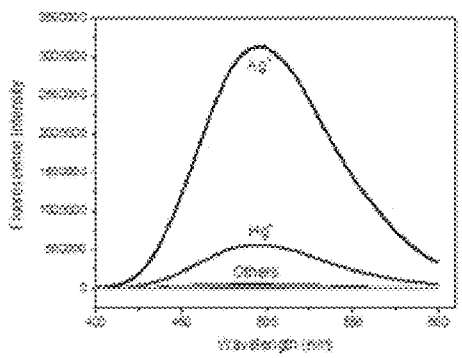
FIGS. 6A-6B are graphs depicting selective response of TPE-4TTZ.
Figure 6B:
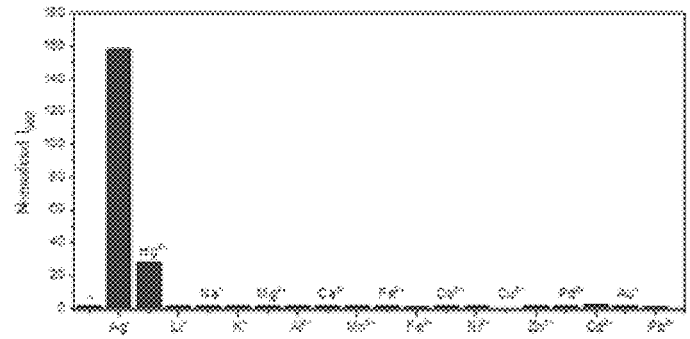

As selectivity is an important parameter for sensing technique, responses of these probes to other metal ions were examined. FIGS. 6A-6B illustrate that besides silver ions, mercury ions induced significant enhancement of PL intensity in phosphate aqueous solution (10 mM, pH 7.4) of TPE-4TTZ, but at a much less visible level than that induced by silver ions. Mercury is reported to coordinate with the tetrazole group. Other metal ions including $Mg^{2+}$, $Mn^{2+}$, $Zn^{2+}$, $Al^{3+}$ etc. hardly increased the PL intensity from TPE-4TTZ at the same conditions. We also observed that $Fe^{2+}$, $Fe^{3+}$, $Co^{2+}$ and $Cu^{2+}$ can quench the weak fluorescence of TPE-4TTZ. Similar results were observed for other tetrazole-tagged TPEs.

The $Ag^+$/$Hg^{2+}$ coordination-induced fluorescence can be pH-sensitive. For example, with respect to TPE-4TTZ, a series of tests were done in phosphate buffer solutions at different pH varying from 4 to 12. At pH lower than 4, the tetrazole moiety (pKa~4-5) was largely in the protonated form and sparingly soluble in solution and, thus, aggregated. The aggregation elicited fluorescence with a different color from that of the silver complexes. Therefore, the turn-on detection is only possible in solutions with pH>4. When pH is from 5~6, PL response is significant enough for a high resolution detection of silver ions. To be noticed, when pH>6, the maximum PL response is relatively stable which demonstrates that the system is a robust sensing system for neutral to basic solutions. Furthermore regarding the mercury detection, the FL response was significant only at the pH window (4~7); when pH>8, the fluorescence turn-on was not observed anymore. Thus, TPE-4TTZ is only sensitive to silver ions in basic solutions. Similar observations were made for the other tetrazole-tagged TPEs.

Figure 8:
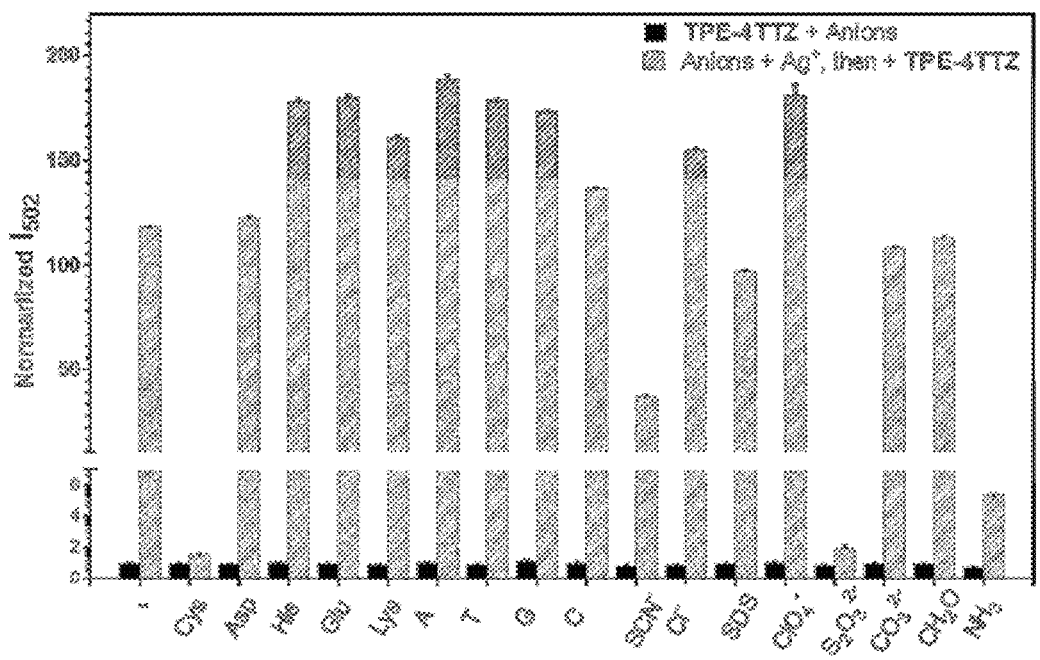
FIG. 8 is a graph showing probes that can snatch silver ions attaching to silver-binding reagents (e.g., Asp, His, Glu, Lys) and elicit a fluorescence turn-on; black columns indicate mixing of TPE-4TTZ (5 μM) with different anions (100 equiv.) did not generate strong fluorescence; gray column shows the fluorescent responses of addition of TPE-4TTZ into pre-mixed anion-Ag$^+$ solutions (10 equiv.); the Y values ($I_{502}$) are normalized against the intensity of TPE-4TTZ in phosphate aqueous solutions (pH 7.4), and thus are close to the enhanced ratio.

Detection can be based on selective coordination involving electrostatic interactions. Tests were conducted to determine whether silver binding moieties (e.g., anions) might be another kind of interfering factor in the mixture. In the test, silver ions were first mixed with the suspected interfering reagents (100 eq.) respectively including most anions, DNA/RNA bases and amino acids. After a short while of shaking, the probe (10 eq.) was added. Each solution was gently mixed and then checked in a PL machine. Compared with the control group, the interfering reagents including amino acids and DNA/RNA bases were only weakly interfering with the silver-tetrazole sensing process. In other words, the tetrazole anions can snatch silver ions from these ligands and elicit a fluorescence turn-on. There were exceptions, in particular for strong silver-interacting structures. Cysteine, the sulfur-containing amino acid, blocked sensing by the strong S—Ag interaction. Similar results were seen from SCN⁻ and $S_2O_3^{2-}$, due to their stronger binding affinity towards $Ag^+$ than the tetrazole anion ($CN_4^-$). In addition, ammonium solution blocked sensing by reducing $Ag^+$ into metallic silver. The results, provided in FIG. 8, suggest that the current silver sensing can be efficient in applications involving silver species, for example biological silver staining.

Monitoring of Silver Ions Released from Metallic Silver

A method of monitoring release of silver ions from metallic silver can include providing a sample comprising metallic silver in a medium, adding one or more of the tetrazole-functionalized AIE luminogens to the medium, and conducting fluorescence imaging of the sample while the compound is in the medium to monitor the release of silver ions from the sample. The sample can be selected from a surface coating, a silver nanomaterial, and a drug. In an embodiment, the compound aggregates as insoluble fluorescent nanoparticles when silver ions are present.

Figure 9A:
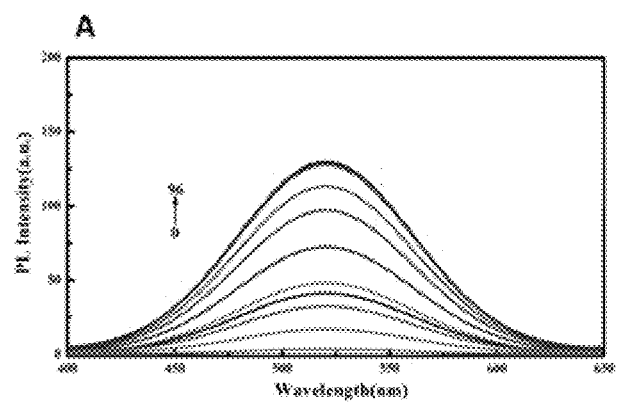
FIG. 9A shows fluorescence spectra of TPE-4TTZ in the presence of AgNWs (500 μg L$^{-1}$) of different time points (from 0 to 96 h) in SM7 medium, excitation: 365 nm.

The present compounds can sense silver ions instantaneously while being non-sensitive towards metallic silver. This property is ideal for monitoring of silver release from metallic silver. The TPE-4TTZ dye was tested to determine the dissolution kinetics of silver nanowires (AgNWs, 500 µg $L^{-1}$) in SM7 medium. After the addition of the TPE-4TTZ probe to the fresh silver nanowire sample, the mixture was repeatedly monitored by PL machine at certain time-points. As shown in FIG. 9A, a turn-on fluorescence was increased with time. By referring to a calibration curve for [$Ag^+$]-fluorescence quantification, the $Ag^+$ release kinetics was depicted (FIG. 9B), which correlated well with traditional methods using conventional ultrafiltration followed by ICP-MS detection. The AIE fluorescence response was able to catch up with the release of silver ions, showing only a slightly slower half-life than ICP-MS quantification. These results further demonstrated that the proposed AIE detection can be used to accurately monitor the dissolution process of AgNWs. In addition, the monitoring by TPE-4TTZ using the same sample is straightforward and much easier to operate as compared with the ICP-MS method.

Figures 10A, 10B, 10C:
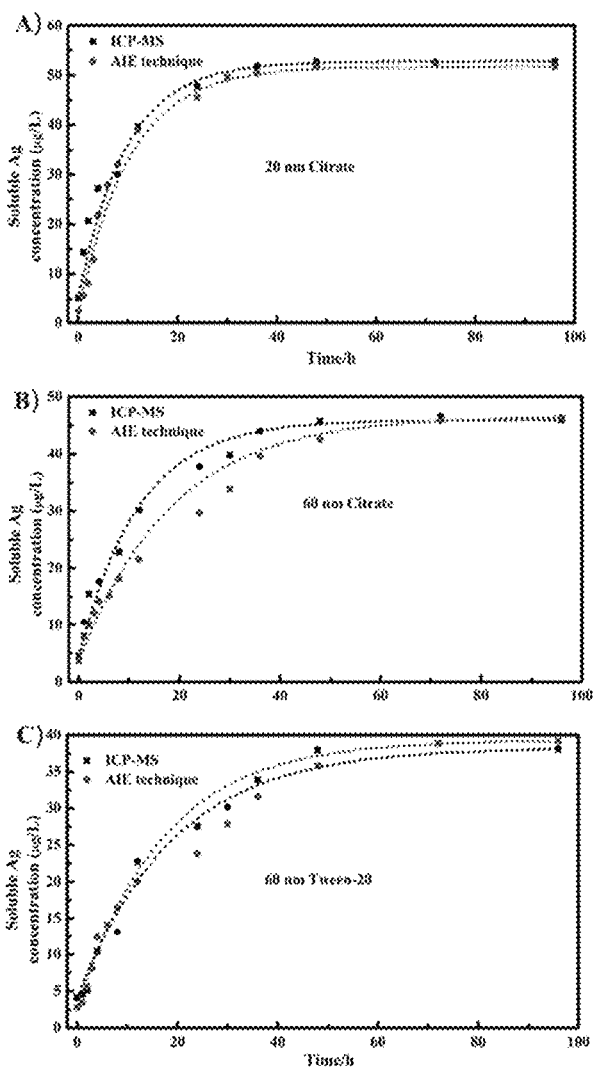
FIGS. 10A-10C depict graphs showing time-course monitoring of silver ion release from silver nanomaterials of different sizes and with different capping reagents (FIG. 10A: Ag nanoparticles (500 μg L$^{-1}$) in SM7 medium.

The release of silver ions can be affected by many factors including the capping reagent and the size/shape of the metallic silver. The fluorescent method works well in these different cases. The silver sensing method described herein using the present compounds can be applied for various silver nanomaterials for monitoring their silver ion release profile at different conditions. As depicted in FIGS. 10A-10C, the silver release kinetics is successfully reflected by this method, and furthermore is consistent with the results by the ICP-MS detection after ultrafiltration (Table 2).

TABLE 2

Dissolution half-life and ultimate silver ion concentration of different NPs using the ICP-MS method and the new method using TPE-4TTZ.

| Entry | Surface | Size (d) | Half-life of release | | [Ag⁺] at equilibrium | |
|---|---|---|---|---|---|---|
| | | | TPE-4TTZ | ICP-MS | TPE-4TTZ | ICP-MS |
| 1 | Citrate | 20 nm | 5.7 h | 4.7 h | 35.5 h | 31.3 h |
| 2 | Citrate | 60 nm | 13.2 h | 6.8 h | 55.9 h | 44.6 h |
| 3 | Tween-20 | 60 nm | 13.8 h | 12.3 h | 55.8 h | 48.1 h |

Fluorescent Silver Staining for In-Gel Detection of Proteins and Other Biological Molecules A method of in-gel detection and separation of biological molecules in a sample can include conducting gel electrophoresis to separate the biological molecules in the sample; staining the separated biological molecules with silver ions; staining the biological molecules with one or more of the tetrazole-functionalized AIE luminogens after staining with silver ions; and conducting fluorescence imaging of the separated biological molecules after staining with the tetrazole-functionalized AIE luminogens. At least one of the biological molecules can be selected from proteins, nucleic acids, lipopolysaccharides, glycoproteins and polysaccharides.

In biological labs, silver staining has been routinely used for detection and separation of biological molecules. Silver staining is highly sensitive and, compared to other types of stainings, is generally considered to provide the best detection limits (for example LOD in SDS-PAGE Protein, 0.25 ng per band). Silver ions interact and bind selectively with biological functional groups including carboxyl groups, thiol-containing groups, and amine groups. In natural proteins, the strongest interactions occur with carboxylic acid groups (Asp and Glu), imidazole (His), sulfhydryls (Cys), and amines (Lys).

Figure 12A:
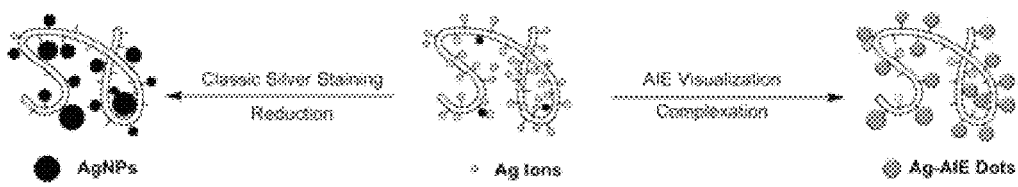
FIG. 12A is a diagram depicting fluorescent staining steps for in-gel detection of proteins and steps classic silver staining steps using a commercial fluorescent protein dye to provide visualization of silver ions by reduction.

For classic silver staining, samples are first impregnated with $Ag^+$, which are then reduced to metallic silver, resulting in a brown-black color to be visualized (FIG. 12A). The chromogenic process is due to the formation of silver nanoparticles (d>10 nm). Thus the silver staining protocols are generally challenging to ensure high stability. Additionally, various sensitizer and enhancer reagents are essential for controlling the specificity and efficiency. Classic protocols of silver staining use either glutaraldehyde or formaldehyde as the enhancer. These reagents can cause chemical crosslinking of the proteins in the gel matrix, limiting compatibility with de-staining and elution methods for analysis by mass spectrometry (MS). Nonetheless, staining using fluorescent dyes is common in biological labs because it is generally fast and easy to carry out.

Figure 12B:
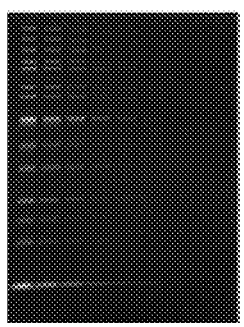
FIG. 12B depicts fluorescent staining results achieved by a commercial fluorescent dye.
Figure 12C:
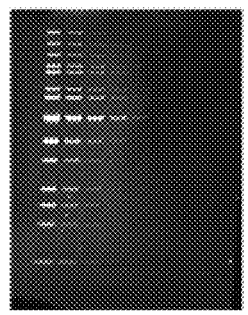
FIG. 12C depicts fluorescent staining results for in-gel detection of proteins using the AIE-active silver probe TPE-4TTZ.

Classic silver staining using SYPRO® Ruby stain (FIG. 12B) was compared with staining using the present compounds in the visualization step of SDS-PAGE electropherosis (fluorescent silver staining in-gel detection method) (FIG. 12C). A preliminary solution test demonstrated that the probes can snatch silver ions prior to attachment to silver-binding amino acids (e.g., Asp, His, Glu, Lys) and elicit a fluorescence turn-on. Here, in combination with the sensitive silver staining & fluorescent imaging technique, the new staining can sense protein bands in SDS-PAGE gel in a similar format (FIG. 12C).

Figure 11:
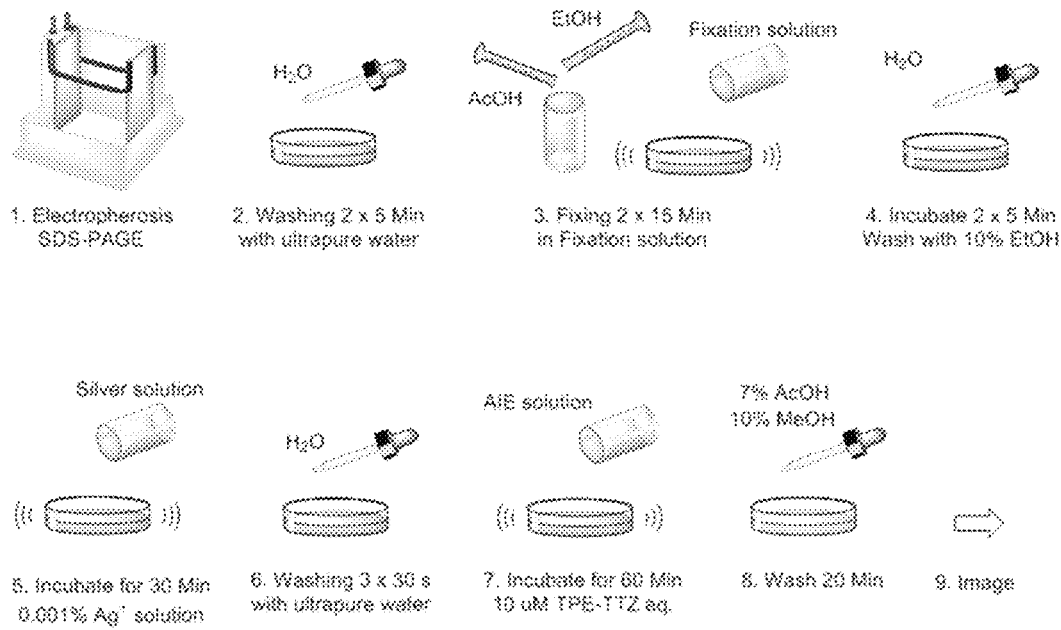
FIG. 11 depicts a flow chart of fluorescent silver staining for in-gel detection of proteins according to the present teachings.

A procedure flow chart for the fluorescent silver staining in-gel detection method is depicted in FIG. 11. The whole process can be completed in about 2-24 hours. As shown in FIG. 12C, the protein bands are clearly visualized in the fluorescent image by using the present method. Although the fluorescent detection limit is estimated to be <1.25 ng protein per band when commercial ladder proteins are used, it is possible that the staining protocol can achieve a 1 pg per band through optimization.

Apart from a higher sensitivity, the fluorescent silver staining protocol according to the present teachings has practical advantages compared to the conventional silver staining (FIG. 12B). Because no chemical modification occurs in the protocol, excised protein bands can be completely destained by sodium thiosulfate (data not shown) and the proteins recovered for analysis by mass spectrometry or sequencing. The protocol is also simple and easy to carry out. Furthermore, this general fluorescent silver staining protocol can be used similarly for the in-gel detection of many biological molecules including proteins, nucleic acids, lipopolysaccharides, glycoproteins and polysaccharides.

The present teachings are illustrated by the following examples.

EXAMPLES

Example 1

Synthesis

Synthesis of Tetraphenylethylene (TPE). Zinc dust (7.2 g) and dry THF (80 mL) were added into a two-necked round-bottom flask, which was vacuumed and purged with dry nitrogen 3 times. $TiCl_4$ (6 mL) was then injected slowly into the flask over a period of 30 minutes. The ice-water bath was removed and the reaction mixture was refluxed for about 2 h. Benzophenone (5.0 g) was dissolved in dry THF (20 mL) and was added into the mixture slowly with a syringe. The mixture was refluxed overnight under nitrogen. After cooling to room temperature, the reaction mixture was quenched with (2 w %) HCl aqueous solution and was extracted with ethyl acetate and water (2×200 mL). The combined organic extracts were washed with distilled water, dried with anhydrous magnesium sulfate and filtered. The solvent was removed with a rotary evaporator. The crude product was washed with ethanol and filtered to yield a white crystalline solid (3.7 g, 80%). $^1$H NMR ($CDCl_3$, 400 MHz) δ 7.05-7.08 (m, 8H), 7.10-7.13 (m, 12H); $^{13}$C NMR ($CDCl_3$, 100 MHz) δ 126.6, 127.8, 131.5, 141.1, 143.9.

Synthesis of Tetra(4-bromophenyl)ethylene (TPE-4Br). In a two-necked round bottom flask, tetraphenylethylene (2 g) was dissolved with glacial acetic acid (30 mL) in an ice-bath. Bromine (5 mL) was injected into the solution with a syringe over a 10 minute period followed by addition of dichloromethane (20 mL). After 15 minutes, the ice-water bath was removed and the resulting mixture was heated at 50° C. for about 15 minutes. The reaction mixture was added to 200 mL ice water, and the precipitated solid was filtered and washed repeatedly with water and ethanol until a light yellow color appeared. The yield of crude product was 1.65 g (43%). The product was used directly without further purification. $^1$H NMR ($CDCl_3$, 500 MHz): δ (ppm) 7.27 (d, J=8.5 Hz, 8H) and 6.85 (d, J=8.5 Hz, 8H).

Synthesis of Tetra(4-cyanophenyl)ethylene (TPE-4CN). TPE-4Br (6.67 g), CuCN (5.0 g, 56 mmol), and DMF (50 mL) were added into a two-necked round bottom flask. The mixture was heated at reflux for 60 hours under nitrogen conditions and then suspended into 300 mL of water. After ethylenediamine (10 mL) was added, the resulting mixture was stirred at 100° C. for 1 hour and was then filtered. The precipitated solid was extracted with dichloromethane (3×150 mL) and the combined organic phase was dried with anhydrous magnesium sulfate. After filtration and solvent evaporation, the residue was repeatedly purified by silica gel column chromatography with hexane and dichloromethane (v/v, 1/1) as eluent to give TPE-4CN 3.1 g in 70% yield as a white solid. $^1$H NMR ($CDCl_3$, 500 MHz): δ (ppm) 7.48 (t, J=5.0 Hz, 8H) and 7.08 (t, J=5.0 Hz, 8H). HRMS (MALDI-TOF), m/z calcd. for $C_{30}H_{16}N_4$: 432.1375; found 432.1379.

Synthesis of TPE-4TTZ. Into a 25 mL round-bottomed flask were added sodium azide (1.12 g, 16 mmol), zinc bromide (450 mg, 2 eq.) and 2 mL of water. TPE-4CN (2 mmol) was dissolved in 10 mL of N-Methylpyrrolidone (NMP) and injected into the solution. The reaction mixture was refluxed for 24 hours with vigorous stirring at 150° C. The mixture was acidified to pH 1 with aqueous HCl solution (3 M) and was extracted into an organic layer with ethyl acetate (20 mL). The organic phase was washed with 3M HCl (2×10 mL) and solvent was evaporated to yield a crude product. This crude product was added into NaOH solution (0.25 M, 40 mL) and stirred vigorously until a white precipitate of zinc hydroxide was observed. The resulting suspension was filtered to remove zinc hydroxide. The filtrate was washed with ethylacetate (10 mL×2) and acidified to pH 1 with 3 M HCl. The tetrazole product precipitated upon stirring, which was again extracted into 20 mL ethyl acetate and the organic layer was separated. The aqueous layer was washed with ethyl acetate (20 mL×2). The organic layers were combined, concentrated and dried under vacuum to yield TPE-4TTZ (71%) as a yellowish solid. $^1$H NMR (400 MHz, DMSO): δ 7.89 (d, 8H, J=8.2 Hz), 7.31 (d, 8H, J=8.2 Hz). HRMS (MALDI-TOF), m/z calcd. for $C_{30}H_{20}N_{16}Na^+$: 627.1949; found 627.1986 (M+Na$^+$).

Synthesis of TPE-2Br. A solution of 2.2 M n-butyllithium in hexane (10 mL) and a solution of diphenylmethane (3.36 g, 20 mmol) in anhydrous tetrahydrofuran (50 mL) were added into a round-bottomed flask at 0° C. under an argon atmosphere. After stirring for 1 hour, bis(4-bromophenyl)methanone (5.4 g, 17 mmol) was added and the reaction mixture was allowed to warm to room temperature with stirring during a 10 hour period. The reaction was quenched with the addition of 10% sodium bicarbonate solution. The mixture was extracted with dichloromethane (3×50 mL) and the combined organic layers were dried with anhydrous magnesium sulfate. The solvent was evaporated to get the resulting crude alcohol. The crude alcohol was dissolved in 80 mL of toluene in a 100 mL flask. A catalytic amount of p-toluenesulfonic acid (0.68 g) was added and the mixture was refluxed for 12 hours. After the resulting mixture was cooled to room temperature, the toluene layer was washed with 10% aqueous sodium bicarbonate solution (2×25 mL) and dried over anhydrous magnesium sulfate and evaporated to afford the crude tetraphenyl-ethylene derivative (TPE-2Br, 3.6 g, 46%). HNMR (300 MHz, CDCl3) δ (ppm): 6.82-6.90 (m, 4H), 6.95-7.05 (s, 4H), 7.06-7.16 (s, 6H), 7.18-7.27 (m, 4H). CNMR (75 MHz, CDCl3) δ (ppm): 120.93, 127.10, 128.10, 131.30, 133.20, 138.55, 142.38, 143.40. HRMS (MALDI-TOF), m/z calcd. for $C_{26}H_{18}Br_2$: 489.9755; found 489.9713.

Synthesis of TPE-2CN. TPE-2Br (975 mg, 2 mmol), CuCN (560 mg), and DMF (10 mL) were added into a two-necked round bottom flask. The mixture was heated at reflux for 60 hours under nitrogen condition and then suspended into 300 mL water. After ethylenediamine (10 mL) was added, the resulting mixture was stirred at 100° C. for 1 hour and was then filtered. The precipitated solid was extracted with dichloromethane (3×150 mL) and the combined organic phase was dried with anhydrous magnesium sulfate. After filtration and solvent evaporation, the residue was repeatedly purified by silica gel column chromatography with hexane and dichloromethane (v/v, 1/1) as eluent to give TPE-2CN in 53% yield. $^1$H NMR (400 MHz, $CDCl_3$): δ 7.45-7.42 (dm, 4H), 7.31 (m, 2H), 7.21-7.14 (m, 8H), 7.11 (dm, 4H). HRMS (MALDI-TOF), m/z calcd. for $C_{28}H_{18}N_2$: 382.1470; found 382.1496.

Synthesis of TPE-2TTZ. Into a 25 mL flask were added sodium azide (300 mg), zinc bromide (450 mg) and 0.5 mL of water. TPE-2CN (250 mg) was dissolved in 4.5 mL of N-Methylpyrrolidone (NMP) and injected into the solution.

The reaction mixture was stirred at 150° C. overnight. The mixture was acidified to pH 1 with aqueous HCl solution (3M) and was stirred vigorously for 30 minutes. The organic mixture was extracted with ethyl acetate (20 mL×2), washed with 3M HCl (50 mL×2) and concentrated to yield a crude product. This crude product was added into NaOH solution (0.25M, 40 mL) and stirred vigorously until a white precipitate of zinc hydroxide was observed. The resulting suspension was filtered to remove zinc hydroxide. The filtrate was washed with ethylacetate (10 mL×2) and acidified to pH 1 with 3 M HCl. The tetrazole product precipitated upon stirring, which was again extracted into 20 mL ethyl acetate and the organic layer was separated. The aqueous layer was washed with ethyl acetate (20 mL×2). The organic layers were combined, concentrated, and dried under vacuum to yield pure product (82%). $^1$H NMR (400 MHz, CDCl$_3$): δ (TMS, ppm) 9.92 (s, 1H), 7.51-7.45 (m, 5H), 7.35-7.34 (m, 2H), 7.25-7.23 (m, 3H), 3.84 (s, 3H). $^{13}$C NMR (100 MHz, CDCl3): δ (TMS, ppm) 181.73, 142.42, 140.68, 135.09, 132.63, 129.83, 129.00, 128.64, 127.72, 126.79, 126.48, 32.28. HRMS (MALDI-TOF), m/z calcd. for $C_{26}H_{19}Br$: 410.0670; found 410.0677.

Synthesis of (2-(4-bromophenyl)ethene-1,1,2-triyl)tribenzene (TPE-Br). A solution of 2.5 M n-butyllithium in hexane (10 mL) and a solution of diphenylmethane (3.36 g) in anhydrous tetrahydrofuran (50 mL) were added into a round-bottomed flask at 0° C. under an argon atmosphere. After the resulting orange-red solution was stirred for 1 hour, (4-bromophenyl)(phenyl)methanone (4.4 g) was added and the reaction mixture was allowed to warm to room temperature with stirring during a 6 hours period. The reaction was quenched with the addition of 10% sodium chloride solution. The mixture was extracted with dichloromethane (3×50 mL) and the combined organic layers were dried with anhydrous magnesium sulfate. The solvent was evaporated to get the resulting crude alcohol. The crude alcohol was dissolved in 80 mL of toluene in a 250 mL flask. A catalytic amount of p-toluenesulfonic acid (680 mg) was added and the mixture was refluxed for 12 hours. After the resulting mixture was cooled down to room temperature, the toluene layer was washed with 10% aqueous sodium bicarbonate solution (2×25 mL), dried over anhydrous magnesium sulfate and evaporated to afford the crude tetraphenyl-ethylene derivative (TPE-Br, 63%). $^1$H NMR (400 MHz, CDCl$_3$): δ 6.88 (d, J=8.5 Hz, 2H), 7.00 (m, 6H), 7.09 (m, 9H), 7.20 (d, J=8.5 Hz, 2H); $^{13}$C NMR (100 MHz, CDCl$_3$): δ 120.6, 126.8, 126.8, 126.9, 127.9, 128.0, 128.1, 131.0, 131.42, 131.44, 131.5, 133.2, 139.8, 141.8, 142.9, 143.4, 143.5, 143.6. HRMS (MALDI-TOF), m/z calcd. for $C_{26}H_{19}Br$: 410.0670; found 410.0677.

Synthesis of 4-(1,2,2-triphenylvinyl)benzonitrile (TPE-CN). TPE-Br (820 mg), CuCN (268 mg), and DMF (10 mL) were added into a two-necked round bottom flask. The mixture was heated at reflux for 60 hours under nitrogen condition and then suspended into 300 mL water. After ethylenediamine (10 mL) was added, the resulting mixture was stirred at 100° C. for 1 hour and was then filtered. The precipitated solid was extracted with dichloromethane (3×150 mL) and the combined organic phase was dried with anhydrous magnesium sulfate. After filtration and solvent evaporation, the residue was purified by silica gel column chromatography with hexane and dichloromethane (v/v, 1/1) as eluent to give TPE-CN as white powder in 53% yield. $^1$H NMR (400 MHz, CDCl$_3$): δ 7.40 (d, 2H, J=8.4 Hz), 7.15 (m, 11H), 7.03 (m, 6H). $^{13}$C NMR (100 MHz, CDCl3): δ 149.0, 143.5, 143.0, 142.9, 142.8, 139.3, 132.1, 131.7, 131.4, 131.3, 128.2, 128.0, 127.4, 127.2, 119.2, 110.0. HRMS (MALDI-TOF), m/z calcd. for $C_{30}H_{20}N_{16}Na^+$: 357.1517; found 357.1536.

Synthesis of TPE-1TTZ. Into a 10 mL round-bottomed flask were added sodium azide (138 mg, 2 mmol), zinc bromide (225 mg, 2 mmol) and 0.5 mL of water. TPE-CN (357 mg, 1 mmol) was dissolved in 4.5 mL of N-Methylpyrrolidone (NMP) and injected into the solution. The reaction mixture was stirred at 150° C. The mixture was acidified to pH 1 with aqueous HCl solution (3M) and was stirred vigorously for 30 minutes. The organic mixture was extracted with ethyl acetate (20 mL×2), washed with 3M HCl (50 mL×2) and concentrated to yield a crude product. This crude product was added into NaOH solution (0.25M, 40 mL) and stirred vigorously until a white precipitate of zinc hydroxide was observed. The resulting suspension was filtered to remove zinc hydroxide. The filtrate was washed with ethylacetate (10 mL×2) and acidified to pH 1 with 3 M HCl. The product precipitated upon stirring, which was again extracted into 20 mL ethyl acetate and the organic layer was separated. The aqueous layer was washed with ethyl acetate (20 mL×2). The organic layers were combined, concentrated and dried under vacuum to yield pure product as a white powder (82%). $^1$H NMR (400 MHz, DMSO): δ 7.80 (d, 2H, J=8.4 Hz), 7.20-7.13 (m, 11H), 7.03-6.98 (m, 6H). HRMS (MALDI-TOF), m/z calcd. for $C_{27}H_{20}N_4$: 400.1722; found 400.1762.

Example 2

Silver Ion Detection

Tetrazole-tagged AIE luminogen TPE-4TTZ (5 μM) undergoes a fluorescence turn-on response towards a solution of silver ions. The solutions can include organic solutions, aqueous solutions including natural water, wastes and/or biological buffer solutions. PL spectra were recorded on a Perkin-Elmer LS 55 spectrofluorometer.

With reference to FIGS. 3A-3D and 7, a fluorescent calibration curve for quantification of [Ag$^+$] by the above luminogens (TPE-1TTZ, TPE-2TTZ, TPE-4TTZ) (5 μM) showed good linearity and reproducibility. The solutions included organic solutions, aqueous solutions including natural water, wastes and/or biological buffer solutions. For the same probes, the calibration curve varied a little in different solutions. UV spectra were measured on a Biochrom Libra S80PC double beams spectrometer. PL spectra were recorded on a Perkin-Elmer LS 55 spectrofluorometer.

Figure 7:
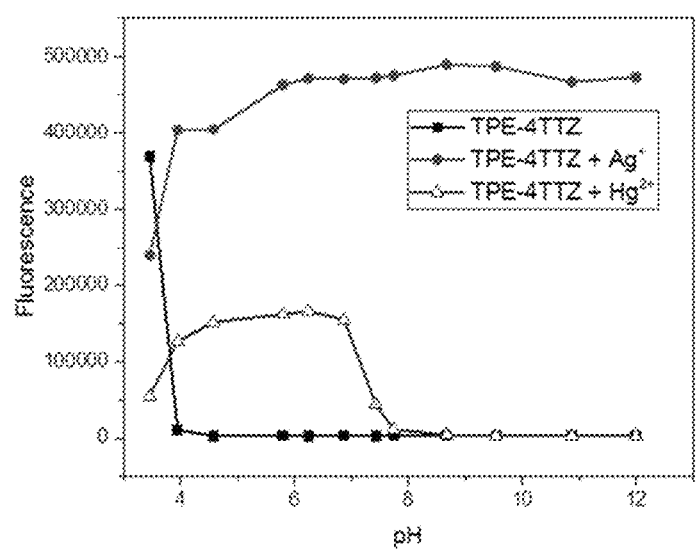
FIG. 7 is a graph depicting fluorescence emission response (502 nm) of TPE-4TTZ (10 μM) in the absence and presence of Ag$^+$ (10 equiv.) and Hg$^{2+}$ (10 equiv.) in aqueous phosphate buffer solution (10 mM) at different pH (Excitation: 350 nm; Filter slits: 1 nm/1 nm).

With reference to FIG. 7, tetrazole-tagged AIE luminogen TPE-4TTZ (10 μM) underwent a fluorescence turn-on response towards a solution of silver ions in the presence of other metal ions in phosphate aqueous solution (10 mM, pH 7.4). PL spectra were recorded on a Perkin-Elmer LS 55 spectrofluorometer. Tetrazole-tagged AIE luminogen TPE-4TTZ (10 μM) underwent a fluorescence turn-on response towards a solution of silver ions in the presence of other silver-binding molecules in phosphate aqueous solution (10 mM, pH 7.4). In each example, the silver-binding molecule was added prior to the addition of the probes from a stock solution. The stock solution of the probe is 1 mM in ethanol. PL spectra were recorded on a Perkin-Elmer LS 55 spectrofluorometer.

Example 3

Monitoring of Silver Ion Release from Materials

Figure 9B:
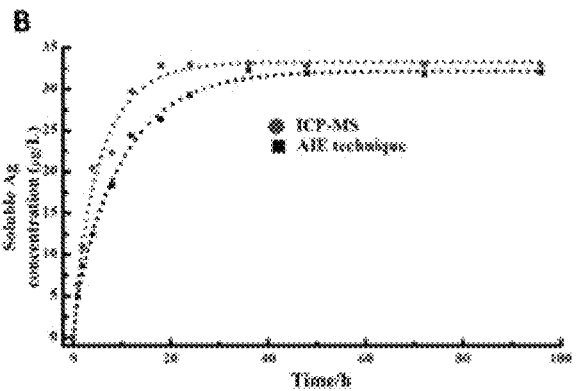
FIG. 9B shows a plot of soluble Ag$^+$ concentrations showing the release kinetics from AgNWs in SM7 medium as detected by conventional ultrafiltration followed with ICP-MS detection and AIE techniques by TPE-4TTZ in FIG. 9A.

With reference to FIGS. 9A-9B, the release kinetics of Ag$^+$ from silver nanowires was determined by these probes.

In a typical case, the AgNPs suspensions (500 µg L$^{-1}$) were added into the SM7 medium containing 3 mM fluorogenic TPE-4TTZ. AgNWs were prepared according to the protocol (*Adv. Mater.*, 2002, 14, 833-837). The synthetic AgNWs were diluted with deionized water and then deposited on silicon substrates, and characterized by Bruker scanning electron microscopy (SEM) equipped with an EDAX attachment. The mixture solution was detected by fluorescence spectrophotometer (Perkin-Elmer LS 55 spectrofluorometer) at different time points (0, 2, 4, 8, 12, 24, 30, 36, 48, 60, 72 and 96 h). For a comparison, the release kinetics was also determined by conventional ultracentrifugation followed with ICP-MS detection. In this conventional method, AgNWs concentrations in SM7 medium were determined by ultracentrifugation through 3 kD membrane (pore size around 1 nm, Millipore, USA). AgNWs suspensions were centrifuged at 4000 rpm for 20 min. After that, the filtrate containing the soluble Ag (nanoparticles were trapped on the membrane), was sampled at different time points (0, 2, 4, 8, 12, 24, 30, 36, 48 and 72 h). The Ag concentrations in the filtrate were measured by ICP-MS.

With reference to FIGS. 13A-13C, the release kinetics of Ag$^+$ from silver nanoparticles with different sizes (20, 60 nm) and different coatings/stabilizers (citrate, tween-20) were determined by these probes. AgNPs were synthesized by following the protocol (*Environ. Sci. Technol.*, 2010, 44, 2169-2175). In a typical case, the AgNPs suspensions (500 µg L$^{-1}$) were added into the SM7 medium containing 3 mM fluorogenic TPE-4TTZ. The mixture was followed by fluorescence spectrophotometer (Perkin-Elmer LS 55 spectrofluorometer) at different time points (0, 2, 4, 8, 12, 24, 30, 36, 48, 60, 72 and 96 h). For a comparison, the release kinetics was also determined by conventional ultracentrifugation followed with ICP-MS detection, similar to the case of AgNWs.

Example 4

Fluorescent Silver Staining of In-Gel Protein Detection

With reference to FIGS. 11, and 12A-12C, a protocol was established to combine the conventional silver staining and the fluorescent silver ion sensing for the detection of proteins after SDS-PAGE (Sodium dodecyl sulfate polyacrylamide gel electrophoresis). In the SDS-PAGE, the reagents/products used included: Thermo Fisher Scientific: Mini Gel Tank (Invitrogen), NuPAGE™ 4-12% Bis-Tris Protein Gels (Catalog number: NP0323BOX), NuPAGE™ MES SDS Running Buffer (Catalog number: NP0002), PageRuler™ Unstained Protein Ladder (Catalog number: 26614), NuPAGE™ Sample Reducing Buffer (Catalog number: NP0004), and NuPAGE™ LDS Sample Buffer (Catalog number: NP0007). The standard protocol available from Thermo Fisher Scientific was followed. After electrophoresis, the fluorescent silver staining was done by the protocol below, with reference to FIG. 11:
1. Fix gels in fixing solution (40% EtOH 7% Acetic acid) 2×1 hour with a change of solution.
2. Wash in ultra-pure water for 2×5 min.
3. Stain in 100 ml of 0.001% AgNO$_3$ (solution must be at room temperature) for 90 minutes.
4. Incubate gels in ultra-pure water for 2×5 min. (with a change of water) to increase the pH of the gel to neutral (test using pH paper) before staining with the AIE compounds (TPE-1TTZ, TPE-2TTZ, TPE-4TTZ).
5. Stain with 10 µM of the AIE compounds for one hour.
6. Rinse gels in water briefly (5 minutes) before imaging.
7. Imaging was carried out on a ProteinSimple instrument (AlphaImager MINI): Both 302 nm and 365 UV channel gave good results.

With reference to FIG. 12B, a similar gel staining using commercial fluorescent imaging dye for comparison was used.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:
1. A fluorescent probe for ionic silver detection, comprising a compound that exhibits aggregation induced emission properties, wherein the compound comprises

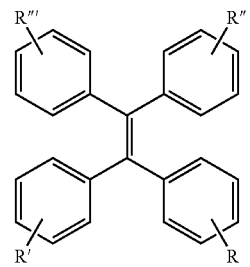

wherein three of R, R', R" or R''' are

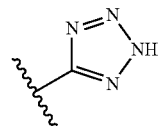 [SMILES: *c1nn[nH]n1]

and one of the of R, R', R" and R''' groups is selected from the group consisting of H, heteroatom, alkyl, unsaturated alkyl, heteroalkyl, cycloalkyl, heterocycloalkyl, and aryl.
2. A method of detecting for presence of silver ions in a solvent, comprising:
   contacting the compound of claim 1 with the solvent, the solvent being selected from the group consisting of natural water, industrial wasters, aqueous buffer solutions and biological samples; and then
   irradiating the solvent with ultraviolet light,
wherein an observable emission indicates the presence of the silver ions.
3. A method of imaging ionic silver in vivo, comprising:
   administering the compound of claim 1 to an organism; and
   obtaining images of the organism while the compound is within the organism using fluorescence imaging.
4. A method of in-gel detection and separation of biological molecules in a sample, comprising:
   conducting gel electrophoresis to separate the biological molecules in the sample;
   staining the separated biological molecules with silver ions;
   staining the biological molecules with the compound of claim 1 after staining with silver ions; and conducting fluorescence imaging of the separated biological molecules after
staining with the compound of claim 1,
wherein at least one of the biological molecules is selected from the group consisting of proteins, nucleic acids, lipopolysaccharides, glycoproteins and polysaccharides.

5. A method of monitoring the release of silver ions from metallic silver, comprising:
providing a sample comprising metallic silver in a medium;
adding the compound of claim 1 to the medium; and
conducting fluorescence imaging of the sample while the compound is in the medium to monitor the release of silver ions from the sample, wherein the sample is selected from the group consisting of a surface coating, a silver nanomaterial, and a drug.

6. The method of claim 5, wherein the compound aggregates as insoluble fluorescent nanoparticles when silver ions are present.

7. A fluorescent probe for ionic silver detection, comprising:
one or more compounds selected from the group consisting of:

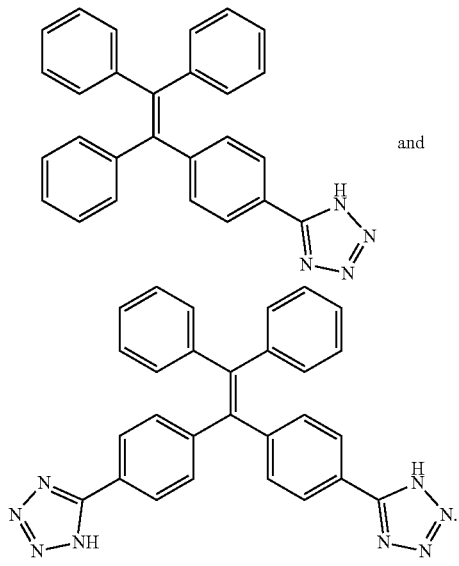

and

8. A method of detecting a presence of silver ions in a solvent, comprising:
contacting the compound of claim 7 with the solvent, the solvent being selected from the group consisting of natural water, industrial wasters, aqueous buffer solutions and biological samples; and
irradiating the solvent with ultraviolet light,
wherein an observable emission indicates the presence of the silver ions.

9. A method of imaging ionic silver in vivo, comprising:
administering the compound of claim 7 to an organism; and
obtaining images of the organism while the compound is within the organism using fluorescence imaging.

10. A method of in-gel detection and separation of biological molecules in a sample, comprising:
conducting gel electrophoresis to separate the biological molecules in the sample;
staining the separated biological molecules with silver ions;
staining the biological molecules with the compound of claim 7 after staining with silver ions, and
conducting fluorescence imaging of the separated biological molecules after staining with the compound of claim 7,
wherein at least one of the biological molecules is selected from the group consisting of proteins, nucleic acids, lipopolysaccharides, glycoproteins and polysaccharides.

11. A method of monitoring the release of silver ions from metallic silver, comprising:
providing a sample comprising metallic silver in a medium;
adding the compound of claim 7 to the medium; and
conducting fluorescence imaging of the sample while the compound is in the medium to monitor the release of silver ions from the sample, wherein the sample is selected from the group consisting of a surface coating, a silver nanomaterial, and a drug.

12. The method of claim 11, wherein the compound aggregates as insoluble fluorescent nanoparticles when silver ions are present.

\* \* \* \* \*